United States Patent [19]

Slamin

[11] Patent Number: 5,152,796
[45] Date of Patent: Oct. 6, 1992

[54] MODULAR KNEE PROSTHESIS

[75] Inventor: John E. Slamin, Wrentham, Mass.

[73] Assignee: Johnson & Johnson Orthopaedics, Inc., Raynham, Mass.

[21] Appl. No.: 713,921

[22] Filed: Jun. 12, 1991

Related U.S. Application Data

[63] Continuation-in-part of Ser. No. 630,419, Dec. 19, 1990, abandoned, which is a continuation of Ser. No. 560,247, Jul. 27, 1990, abandoned, which is a continuation of Ser. No. 290,540, Dec. 27, 1988, abandoned.

[51] Int. Cl.[5] ............................................. A61F 2/38
[52] U.S. Cl. ................................................. 623/20
[58] Field of Search ....................................... 623/20

[56] References Cited

U.S. PATENT DOCUMENTS

| 4,187,559 | 2/1980 | Grell et al. | 623/20 |
| 4,822,365 | 4/1989 | Walker et al. | 623/20 |
| 4,822,366 | 4/1989 | Bolesky | 623/20 |

Primary Examiner—David Isabella
Assistant Examiner—Debra S. Brittingham

[57] ABSTRACT

A knee prothesis system which is composed of a femoral component and a series of bolts capable of being attached to the femoral component and extending through the femoral component at different angles. These angles correspond to different valgus angles. The system also includes stems of different lengths and diameters which can be attached to the bolts to provide a system with stems of different and diameter lengths set at different valgus angles.

15 Claims, 3 Drawing Sheets

MODULAR KNEE PROSTHESIS

CROSS REFERENCE TO RELATED APPLICATIONS

This application is a continuation-in-part of application Ser. No. 630,419 filed Dec. 19. 1990 ABN, in turn is a continuation of application Ser. No. 560,247 filed Jul. 27, 1990, now abandoned, which in turn is a continuation of application Ser. No. 290,540 filed Dec. 27, 1988, now abandoned.

BACKGROUND OF THE INVENTION

1. Field of the Invention

The present invention relates to a modular knee prosthesis system, that is a system of implantable prosthesis used to replace a natural knee and which includes a series of intramedullary stems having different configurations including different lengths and different valgus angles. The valgus angle and the stem length and stem diameter can be varied by the surgeon immediately prior to the implantation of the device which allows greater surgical flexibility in the implantation of a total knee prosthesis.

2. Prior Art

Total knee prostheses have been in use for some time. These prostheses generally comprise a tibia component, a femoral component and a patellar component. The femoral component of the prosthesis generally comprises spaced-apart condylar portions and a connector joining the condylar portions. The tibial component of the prosthesis is constructed to receive the condylar portions of the femoral component, that is, the condylar portions are in direct contact and are supported by the tibial component. The femoral contact surface of the tibial component is made from a biocompatible plastic material such as ultra high molecular weight polyethylene. The patellar portion of the prosthesis is generally a ultra-high molecular weight polyethylene button, which may be metal backed or reinforced, and which is affixed to the natural patella and rides in a depression on the metal surface of the femoral component. Typical of such prosthesis is the prosthesis shown in U.S. Pat. No. 4,298,992.

The prostheses of the type shown in the above mentioned patent are generally available with or without an intramedullary stem. The intramedullary stem is used to lend lateral stability to the prosthesis and is inserted into the medullary canal of the femur. The stems are set at an angle to the vertical which duplicates the valgus angle in the human anatomy. The valgus angle is the angle between the center line of the femur and an imaginary vertical line extending from the distal femur to the center of the femoral head. This angle is generally somewhere between 5° and 9°.

When selecting a prosthesis for implantation, the surgeon does not necessarily know the valgus angle precisely and may or may not know whether or not a prosthesis with an intramedullary stem would be desired for the particular patient. It is the general rule of thumb that the least complicated prosthesis which requires the least removal of bone from the patient would be the prosthesis of choice to be implanted.

Modular prosthesis such as those shown in U.S. Pat. Nos. 4,404,691 and 4,578,081 have been proposed. The prosthesis disclosed in these patents have stems or shanks which may be extended in length, but do not provide for a prosthesis with no stem or variation in the valgus angle of the stem.

U.S. Pat. No. 4,822,366 discloses a modular knee prosthesis in which the valgus angle of a femoral stem including a femoral stem extension can be varied to some degree. The configuration of the device requires extensive removal of bone from the distal femur to implant the device.

SUMMARY OF THE INVENTION

The prosthesis of the present invention gives a flexibility to the orthopedic surgeon in providing a single femoral component of a total knee prosthesis. This femoral component is identical for right or left knees and can be varied to accept stems of different diameters, different lengths and set at different valgus angles for use in right or left knees. The system of the present invention allows a surgeon greater flexibility in the implantation of a prosthesis and provides a number of relatively inexpensive components to be available and ready to be implanted during the surgical procedure. The system of the present invention is particularly useful for revision knee surgery. This prosthesis simplifies inventory control systems and the cost of inventory for both the manufacturer and hospital and therefore reduces the costs of such procedures.

DETAILED DESCRIPTION OF THE INVENTION

Figure 1:
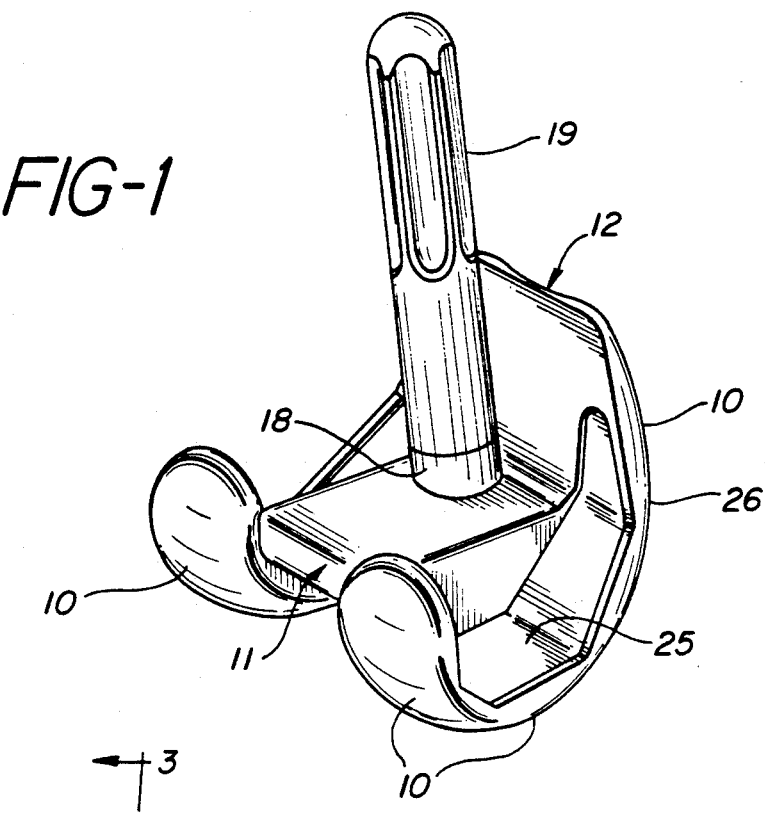
FIG. 1 is an isometric view of the completely assembled prosthesis of the present invention.
Figure 2:
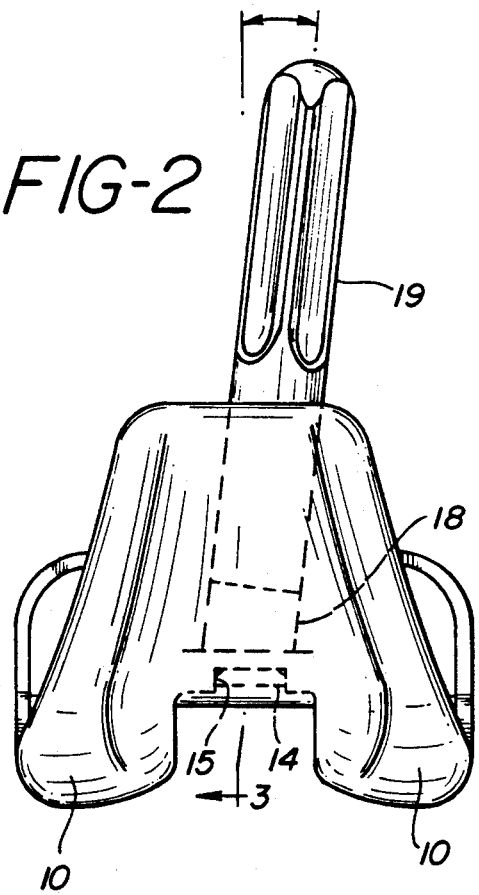
FIG. 2 is a front view showing the prosthesis of the present invention.
Figure 3:
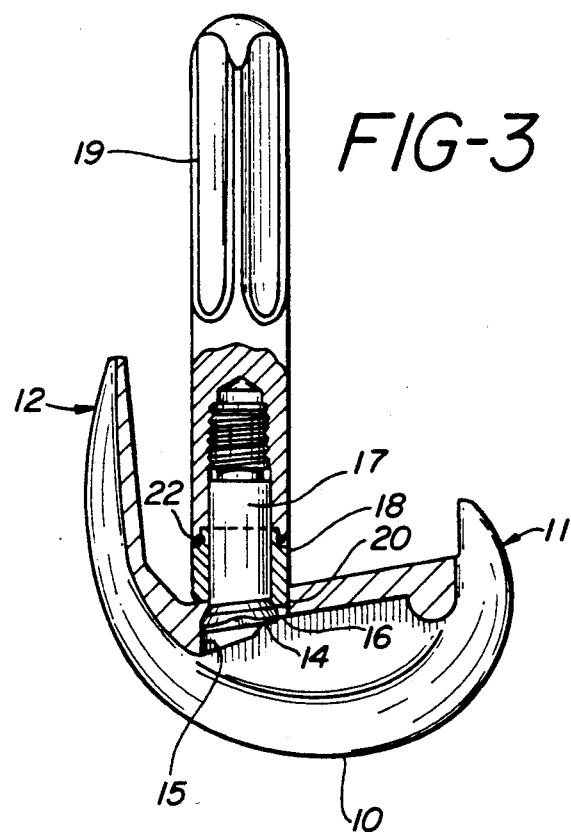
FIG. 3 is a side view, partially in section, of the prosthesis of the present invention.
Figure 4:
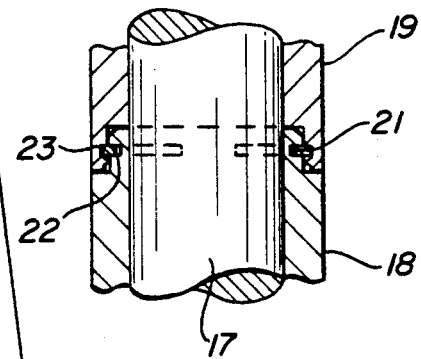
FIG. 4 is an exploded view of a portion of the prosthesis of the present invention.

As shown in FIGS. 1-3, the prosthesis of the present invention consists of a femoral component which has two condylar surfaces 10 which are joined by intercondylar connector 11. The condylar surfaces have a patella depression 12 between the condylar surfaces which allows for the patellar portion of the total knee prosthesis to ride in the depression 12 when the knee is flexed. For purposes of orientation, the inner surface 25 of the prosthesis is referred to as the inferior surface and the outer surface 26 is referred to as the superior surface. The side of the prosthesis having the patella depression 12 is the anterior side of the prosthesis and the opposite side is the posterior side. The portion of the prosthesis including the condylar surfaces and the intercondylar connector may be similar in construction to the prosthesis that is shown in U.S. Pat. No. 4,298,992. In the present prosthesis, there is an aperture 13 which is shown in the drawings as being a circular aperture. This aperture could be a different shape if desired. At the posterior edge of the aperture there is a small opening or slot 16 whose purpose will be subsequently described. The present prosthesis includes a femoral bolt 17 which has the same cross sectional configuration as the aperture and which will fit through the aperture and extend through a stem collar 18 and into the threaded portion of a stem 19. The interior of the stem has a female portion of threads which can be threaded onto the threaded portion of the femoral bolt 17 when the device is assembled. The bolt will be held in position in the aperture as the head 14 of the bolt is wider than the aperture 13. When the stem on the bolt is tightened, the stem collar 18 and the bolt head 14 are drawn toward each other until the bolt head 14 and stem collar 18 are in firm contact with the intercondylar surface thereby holding the stem at the proper valgus angle. The stem collar has a circumferential slot 21 near the end of the collar which can receive a circular clip 22 to lock the stem onto the stem collar. There is a corresponding depression or slot 23 in the stem. As shown in FIG. 4, the clip 22 fits partially into the slot 21 in the stem collar and partially into the slot 23 in the stem to lock the stem onto the stem collar. The femoral bolt has a head 14 which is sized to snugly fit into a recess 15 on the superior surface of the intercondylar connector.

The femoral bolt 17 is constructed with the axis of its shaft at an angle to the head 14 of the bolt which can be seen in FIG. 2. The head of the bolt is also angled so that the surface of the head is relatively flush in the recess 15 in the bottom of the intercondylar box. The stem forms an angle, the valgus angle, with the bottom of the box of from 5°, 7° or 9°. These are the angles that are generally used in stem prosthesis constructions for the valgus angles. The bolt, when it is fully seated in the bottom of the intercondylar box, forms the valgus angle. The stem collar, in order to fit tightly around the bolt, has an angle with the horizontal which corresponds to the valgus angle.

In the modular system of the present invention, bolts are provided in right and left configurations and at angles of 5°, 7° and 9°. For each bolt, there is a corresponding stem collar. The stems are provided in constant but different diameters, usually 13 millimeters and 15 millimeters and of different lengths such as 90 and 130 millimeters. The stem collars are sized to correspond to the diameter of the stem. For each knee, i.e., right or left, there are 12 possible modifications; three different valgus angles each having two possible stem diameters and two possible stem lengths.

Figure 5:
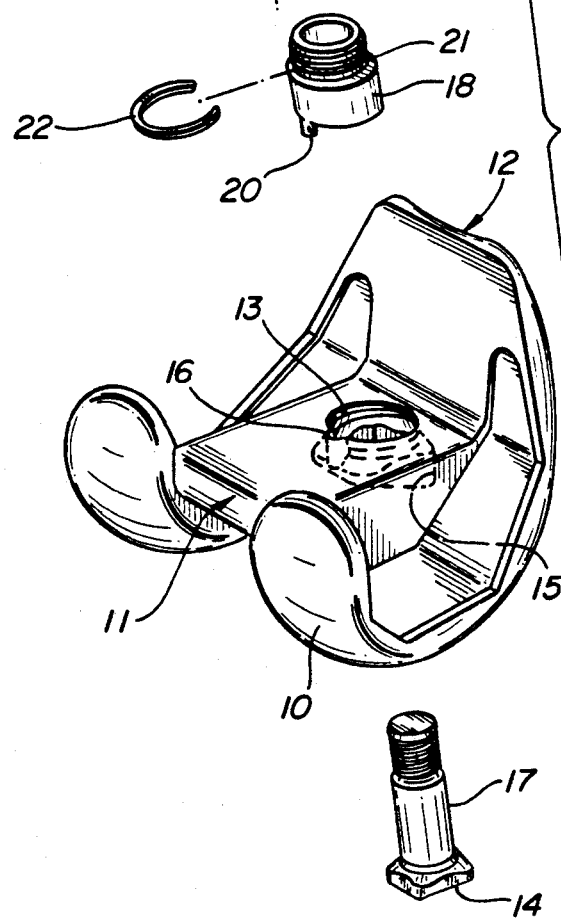
FIG. 5 is an exploded view of the prosthesis of the present invention.
Figure 6:
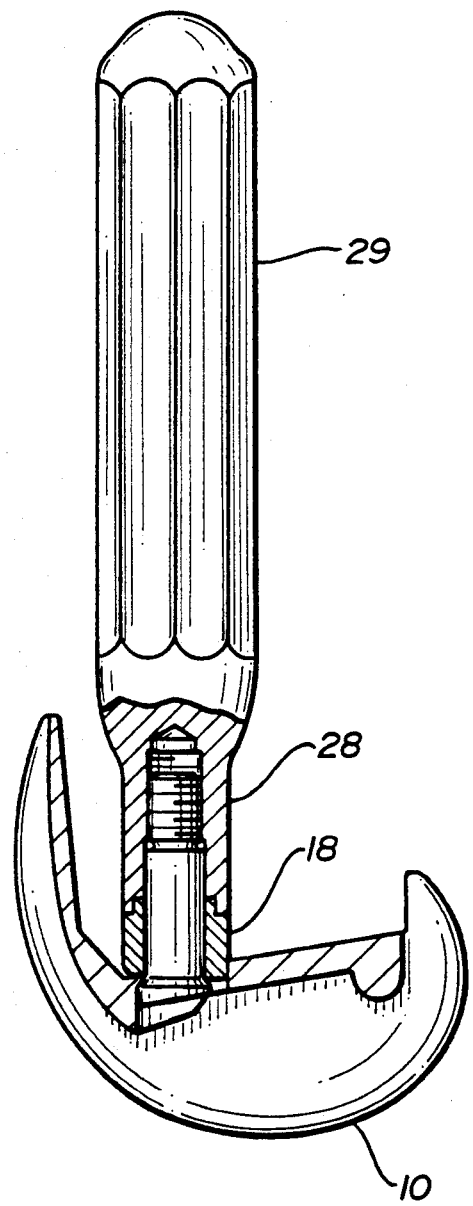
FIG. 6 and FIG. 7 are side views, partially in section, of embodiments of the invention in which there is a variation in the diameter of the stem.
Figure 7:
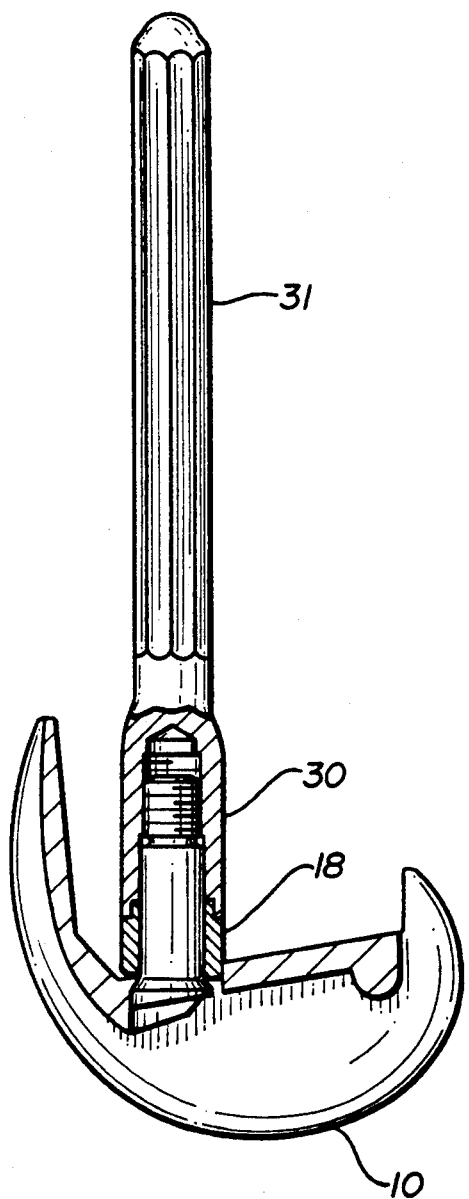

FIG. 6 and 7 show alternate embodiments of the present invention in which there is a variation in the diameter of the stem along its length. The distal portion of the stem 18 is that portion which is in contact with the stem collar and extends proximally a distance which is about equal to the length of the femoral bolt 17. The proximal portion is the remainder of the stem. The purpose of variable diameter stems is to provide stems in which the diameter of the proximal portion may be to varied to more closely correspond to the diameter of the medullary canal of the femur of a particular patient. The diameter of the distal end of a particular stem is sized to correspond to the diameter of a particular stem collar. Therefore, stems which have a constant diameter and stems with proximal portions having diameters larger or smaller than the diameter of the collar can be fitted to the same stem collar. This offers surgeons greater flexibility in construction of a prosthesis to fit the needs of a particular patient. The stem shown in FIG. 6 has a distal end 28 which is the same diameter as the stem collar 18. The proximal portion of the stem 29 has a diameter which is larger than the diameter of the distal portion of the stem 28. In the stem shown in FIG. 6, the ratio of the diameter of the proximal portion (larger diameter) to the distal portion (smaller diameter) may be from about 1 to 1 to about 2 to 1, preferably about 1.3 to 1. The stem shown in FIG. 7 has a distal end 30 which is the same diameter as the stem collar 18. The proximal end 31 of the stem has diameter which is smaller than the diameter of the distal portion of the stem. The ratio of the diameter of the distal (larger diameter) portion to the diameter of the proximal (smaller diameter) portion may be from about 1 to 1 to 2 to 1, preferably about 1.3 to 1. A ratio of 1 to 1 indicates that the stem has a constant diameter along its length. The distal portion of the stems could be the same diameter as the stem collars used with the constant diameter stems, i.e. 10 or 13 millimeters. The proximal portions of the stems would be 10 or 22 millimeters. Other than the variation in the diameter of the stem, the details of the construction of the embodiments of the stems of FIG. 6 and FIG. 7 is the same as that shown in FIG. 4 and FIG. 5.

It should be understood that the basic femoral component design in the present system can be used for either the right or left knee whether or not a stem is used. If the stem is used, it is necessary to have bolts that are inclined to the left or right depending on which knee would be involved. The bolts would also have different valgus angles. If one wanted to have the capability of implanting a prosthesis in either the right or left knee at valgus angles of 5°, 7° or 9° and with stem diameters of 13 or 15 millimeters and stem lengths of 90 or 130 millimeters, it would normally be necessary to have available twelve different prosthesis for the right knee and twelve different prosthesis for the left knee. In the present modular system, one would need only a single femoral component, and would preferably have 12 left knee stem sets and 12 right knee stem sets available for implantation. Since the actual femoral component is the most expensive component, it is not necessary to keep a high cost inventory of this component, but a great number of implant options can be made with the changing of the relatively inexpensive materials such as the femoral bolt, the intramedullary stems and the stem collars. With the use of stems of variable diameter, even more options are available to the surgeon. If the prosthesis of the present invention were selected by an orthopedic surgeon for implantation, the surgeon would have available the correct size of the femoral component and a set of femoral bolts, stems and stem collars. If, during the operative procedure it would appear that a stem would not be needed for the particular patient, the stem, femoral bolt, stem collar would not be used. If it was decided that a stem would be used, the correct valgus angle femoral bolt and stem assembly of the desired diameter and length would be selected. The femoral bolt would then be fitted into the bottom of the femoral component and the stem assembly inserted with the antirotation stud 20 of the stem collar in the slot 16. The antirotation stud 20 sitting in the slot 16 would prevent the rotation of the stem collar when the stem is tightened on the femoral bolt. After the stem was tightened to the bolt, the prosthesis would be ready to implant.

The stems and stem collars can be preassembled at a factory into a stem assembly if desired. Each stem assembly would include a stem and a stem collar of the same diameter as the stem, connected with a circular clip. The preassembly of the stem and stem collars is a convenience to the surgeon. During the surgical procedure, if the surgeon would decide that a stem were to be desirable, he would select the proper bolt and stem assembly, insert the bolt through the aperture 13 and attach the stem assembly to the bolt insuring that the stud 20 is positioned in the slot 16.

I claim:

1. A modular femoral component for a modular knee system, comprising a femoral component with two condylar surfaces joined by an intercondylar connector having an inferior portion and including at least two femoral bolts having a shaft and head, at least one of said bolts constructed with said shaft at an acute angle to said head, each of said bolts adapted to be connected to and fitted into an opening in said intercondylar connector, a recess in a superior surface of the opening, the head of the bolt being shaped so that the head is flush in the recess when the bolt is seated therein and the bolt extending upwardly towards an inferior surface of the femoral component, at least one stem collar adapted to be fitted around the bolt and in contact with the inferior portion of the intercondylar connector, the stem collar and the femoral bolt being fixable into the intercondylar connector at acute angles which correspond to a valgus angle desired in the implanted femoral component, and in which a plane passing along a surface of the stem collar in contact with the inferior portion of the intercondylar connector forms an acute angle with a plane passing along an opposite surface of the stem collar which corresponds to the valgus angle, a series of at least two stems of different lengths, the distal portion of each of said stems having an equal diameter as its associated stem collar and each of said stems being adapted to be fixed to a femoral bolt to form a completed femoral component.

2. The femoral component of claim 1 in which at least one of the bolts is angled to the left of the opening in the intercondylar connection and at least one of the bolts is angled to the right of the opening in the intercondylar connector.

3. The femoral component of claim 1 in which the series of stems includes at least four stems and proximal portions of said stems having at least two different diameters.

4. The femoral component of claim 1 having at least three femoral bolts, each of said bolts having different acute angles thereby extending, when fully seated in the intercondylar connector, at an angle which differs from the angle at which the other bolts extend when fully seated in the intercondylar connector.

5. The femoral component of claim 4 wherein the proximal portion of said stems are of at least two different diameters.

6. The femoral component of claim 5 in which at least one of said bolts is angled to the left of the opening in the intercondylar connector and at least one of said bolts is angled to the right of the opening in the intercondylar connection.

7. The femoral component of claim 1 in which each stem further includes, a connector to connect the stem collar to the stem and in which each stem collar is substantially cylindrical.

8. The femoral component of claim 7 in which the stem is threaded onto the femoral bolt to affix the stem in position.

9. The femoral component of claim 7 in which the femoral bolt extends from the superior surface of the femoral component through a aperture, said aperture having a slot at a posterior edge and said stem collar having a stud on its lower surface which fits into said slot to prevent rotation of the stem collar.

10. The femoral component of claim 1 in which the ratio of the diameter of the distal portion of the stem to the proximal portion of the stem is from 2 to 1 to 1 to 1.

11. The femoral component of claim 1 in which the ratio of the diameter of the proximal portion of the stem to the distal portion of the stem is from 2 to 1 to 1 to 1.

12. The femoral component of claim 1 in which the proximal portion of the stem has the same diameter as the distal portion of the stem.

13. The femoral component of claim 1 in which the proximal portion of a stem has a different diameter than the distal portion of the stem.

14. The femoral component of claim 13 in which the diameter changes of the distal portion of the stem is larger than the diameter of the proximal portion of the stem.

15. The femoral component of claim 13 in which the diameter of the proximal portion of the stem is larger than the diameter of the distal portion of the stem.

* * * * *